(12) United States Patent
Torrie et al.

(10) Patent No.: US 10,660,632 B2
(45) Date of Patent: May 26, 2020

(54) CANNULA

(75) Inventors: Paul Alexander Torrie, Marblehead, MA (US); Victor Manuel Ilizaliturri, Mexico City (MX)

(73) Assignee: Smith & Nephew, Inc., Memphis, TN (US)

( * ) Notice: Subject to any disclaimer, the term of this patent is extended or adjusted under 35 U.S.C. 154(b) by 810 days.

(21) Appl. No.: 12/340,816

(22) Filed: Dec. 22, 2008

(65) Prior Publication Data

US 2009/0163770 A1 Jun. 25, 2009

Related U.S. Application Data

(60) Provisional application No. 61/015,960, filed on Dec. 21, 2007.

(51) Int. Cl.
| | | |
|---|---|---|
| *A61B 1/00* | (2006.01) |
| *A61B 17/02* | (2006.01) |
| *A61B 17/34* | (2006.01) |
| *A61B 17/17* | (2006.01) |
| *A61B 17/32* | (2006.01) |

(52) U.S. Cl.
CPC ........ *A61B 17/025* (2013.01); *A61B 17/3421* (2013.01); *A61B 17/1742* (2013.01); *A61B 2017/0275* (2013.01); *A61B 2017/320044* (2013.01)

(58) Field of Classification Search
CPC .............. A61M 29/00; A61M 25/0068; A61M 25/0194; A61M 25/0662; A61F 2/0805; A61F 2/4601; A61F 2/46; A61B 17/88; A61B 17/17; A61B 17/42; A61B 1/32; A61B 2017/320044; A61B 2017/320056; A61B 17/3417; A61B 2017/3456; A61B 17/1757; A61B 17/320036; A61B 1/303; A61B 17/3421; A61B 1/00135; A61B 1/01; A61B 1/31; A61B 17/025; A61B 17/1742; A61B 2017/0275
USPC .................................. 600/114, 184; 604/264
See application file for complete search history.

(56) References Cited

U.S. PATENT DOCUMENTS

| 2,575,253 | A | * | 11/1951 | Bicek ............................ 600/210 |
| 2,829,649 | A | * | 4/1958 | Glenner ........................ 606/201 |
| 4,350,151 | A | * | 9/1982 | Scott ............................. 600/225 |
| 4,461,281 | A | * | 7/1984 | Carson .......................... 600/104 |
| 4,799,495 | A | * | 1/1989 | Hawkins et al. ............. 600/567 |
| 4,927,424 | A | * | 5/1990 | McConnell et al. ............ 606/96 |

(Continued)

FOREIGN PATENT DOCUMENTS

| DE | 4336989 A1 | 10/1993 |
| EP | 1787592 A2 | 5/2007 |

(Continued)

OTHER PUBLICATIONS

International Search Report and Written Opinion for PCT/US2008/087197 dated Feb. 26, 2009.

(Continued)

*Primary Examiner* — Katrina M Stransky
*Assistant Examiner* — Erin L Colello
(74) *Attorney, Agent, or Firm* — Norman F. Hainer, Jr.

(57) ABSTRACT

The present disclosure relates to a cannula. The cannula includes a shaft having a distal end and a proximal end and a handle coupled to the proximal end of the shaft. The distal end of the shaft includes a tip having a spherical radius.

16 Claims, 3 Drawing Sheets

(56) References Cited

U.S. PATENT DOCUMENTS

| | | | | |
|---|---|---|---|---|
| 5,029,573 | A * | 7/1991 | Chow | 600/104 |
| 5,273,024 | A * | 12/1993 | Menon et al. | 600/114 |
| 5,429,117 | A * | 7/1995 | McNamara et al. | 600/104 |
| 5,658,289 | A * | 8/1997 | Boucher et al. | 623/13.14 |
| 5,902,231 | A * | 5/1999 | Foley et al. | 600/114 |
| 5,913,818 | A * | 6/1999 | Co et al. | 600/204 |
| 6,033,361 | A * | 3/2000 | Co et al. | 600/210 |
| 6,042,538 | A | 3/2000 | Puskas | |
| 6,139,489 | A * | 10/2000 | Wampler et al. | 600/109 |
| 6,193,653 | B1 * | 2/2001 | Evans et al. | 600/210 |
| 6,196,968 | B1 * | 3/2001 | Rydin et al. | 600/210 |
| 6,217,509 | B1 * | 4/2001 | Foley et al. | 600/114 |
| 6,228,024 | B1 * | 5/2001 | Co et al. | 600/204 |
| 6,413,208 | B1 * | 7/2002 | Schollhorn | A61B 17/00008 600/131 |
| 6,428,473 | B1 * | 8/2002 | Leonard et al. | 600/219 |
| 6,450,952 | B1 | 9/2002 | Rioux et al. | |
| 6,497,654 | B1 * | 12/2002 | Leonard et al. | 600/245 |
| 6,613,065 | B2 * | 9/2003 | Lajtai | 606/190 |
| 6,648,815 | B2 * | 11/2003 | Schoellhorn et al. | 600/164 |
| 6,663,605 | B2 * | 12/2003 | Chan | 604/263 |
| 6,746,483 | B1 * | 6/2004 | Bojarski et al. | 623/13.14 |
| 6,929,606 | B2 * | 8/2005 | Ritland | A61B 17/1757 600/201 |
| 6,951,538 | B2 * | 10/2005 | Ritland | 600/210 |
| 7,063,681 | B1 * | 6/2006 | Peery | A61B 17/3417 600/7 |
| 7,384,393 | B2 * | 6/2008 | Guinan | 600/220 |
| D581,050 | S * | 11/2008 | Cottier | D24/133 |
| D604,842 | S * | 11/2009 | Bisleri | D24/108 |
| 7,704,263 | B2 * | 4/2010 | Morris et al. | 606/148 |
| 7,815,649 | B2 * | 10/2010 | Layne et al. | 606/105 |
| 2002/0068911 | A1 * | 6/2002 | Chan | 604/263 |
| 2002/0077632 | A1 * | 6/2002 | Tsou | 606/90 |
| 2002/0123764 | A1 * | 9/2002 | Lajtai | 606/190 |
| 2003/0220689 | A1 * | 11/2003 | Ritland | A61B 17/1757 623/16.11 |
| 2004/0116843 | A1 | 6/2004 | Chan | |
| 2005/0043805 | A1 * | 2/2005 | Chudik | 623/19.14 |
| 2005/0096645 | A1 * | 5/2005 | Wellman et al. | 606/41 |
| 2006/0173443 | A1 * | 8/2006 | Dritschilo et al. | 604/890.1 |
| 2008/0255600 | A1 * | 10/2008 | Braam | A61B 17/00008 606/190 |
| 2008/0319269 | A1 * | 12/2008 | Longo et al. | 600/235 |

FOREIGN PATENT DOCUMENTS

| | | |
|---|---|---|
| JP | H05-253231 | 10/1993 |
| WO | 2005070154 A2 | 8/2005 |

OTHER PUBLICATIONS

Office Action for corresponding JP application No. 2010-539738 dated Mar. 5, 2013.

Office action issued in corresponding Japanese application No. 2010-539738 dated Nov. 11, 2011.

Office action issued in corresponding Australian application No. 2008340311 dated Mar. 14, 2013.

Office Action for corresponding Australian application No. 2008340311 dated Nov. 19, 2014.

Office Action for corresponding Australian application No. 2008340311 dated Nov. 26, 2014.

Office action received in corresponding Japanese patent application No. 2010-539738 dated Aug. 4, 2014.

Office action received in corresponding Japanese patent application No. 2010-539738 dated Nov. 11, 2015.

* cited by examiner

CANNULA

CROSS-REFERENCE TO RELATED APPLICATIONS

This application claims priority to U.S. Patent Application No. 61/015,960, filed on Dec. 21, 2007, the disclosure of which is incorporated herein by reference in its entirety.

BACKGROUND

Field of Technology

The present disclosure relates to a device for guiding a medical instrument to areas within the body where surgical operations are to be carried out, and more particularly, to a device that minimizes damage to those areas of the body during insertion of the device.

Related Art

Instruments, such as slotted cannulas, are used in the field of arthroscopy, especially hip arthroscopy, in order to facilitate the access for medical instruments to joints where surgical operations are to be carried out. The cannula's geometry is that of a tube with the top portion removed, thus producing a semi-circular cross section. The distal tip of these cannulas is cut off at various angles with the thin cross section radiused. Due to the geometry of the distal tip, the tissue within the surgical area is susceptible to damage when the cannula is introduced by the surgeon.

There is a need for a slotted cannula having a distal tip that minimizes the damage that may be caused when the cannula is introduced by the surgeon.

SUMMARY

In one aspect, the present disclosure relates to a cannula. The cannula includes a shaft having a distal end and a proximal end and a handle coupled to the proximal end of the shaft. The distal end of the shaft includes a tip having a spherical radius. In an embodiment, the spherical radius of the tip is equal to an outer radius of the shaft. In another embodiment, the spherical radius of the tip is not equal to an outer radius of the shaft. In yet another embodiment, the tip includes an edge. In a further embodiment, a radius of the edge is about 0.015 inches. In a yet a further embodiment, the outer radius is about 0.155 inches. In an embodiment, the shaft includes a slot extending from the proximal end to the distal end. In another embodiment, the shaft includes a semi-circular cross section. In yet another embodiment, the shaft includes an inner radius of about 0.125 inches. In a further embodiment, the tip includes a longitudinal axis that is parallel with a longitudinal axis of the shaft.

In another aspect, the present disclosure relates to a method of performing arthroscopic surgery. The method includes providing a cannula having a shaft including a distal end and a proximal end and a handle coupled to the proximal end of the shaft, wherein the shaft comprises a tip having a spherical radius; inserting the cannula into a joint area of the body such that the distal tip is inserted into a tissue surface of the joint; inserting a medical instrument through the cannula and into the joint area; and performing a surgical repair in the joint area.

In an embodiment, the distal tip of the shaft is inserted at an angle α relative to the tissue surface. In another embodiment, the angle α is about 30°. In yet another embodiment, the angle α is greater than about 30°.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings.

DETAILED DESCRIPTION OF THE EMBODIMENTS

The following description of the preferred embodiment(s) is merely exemplary in nature and is in no way intended to limit the disclosure, its application, or uses.

Figure 1:
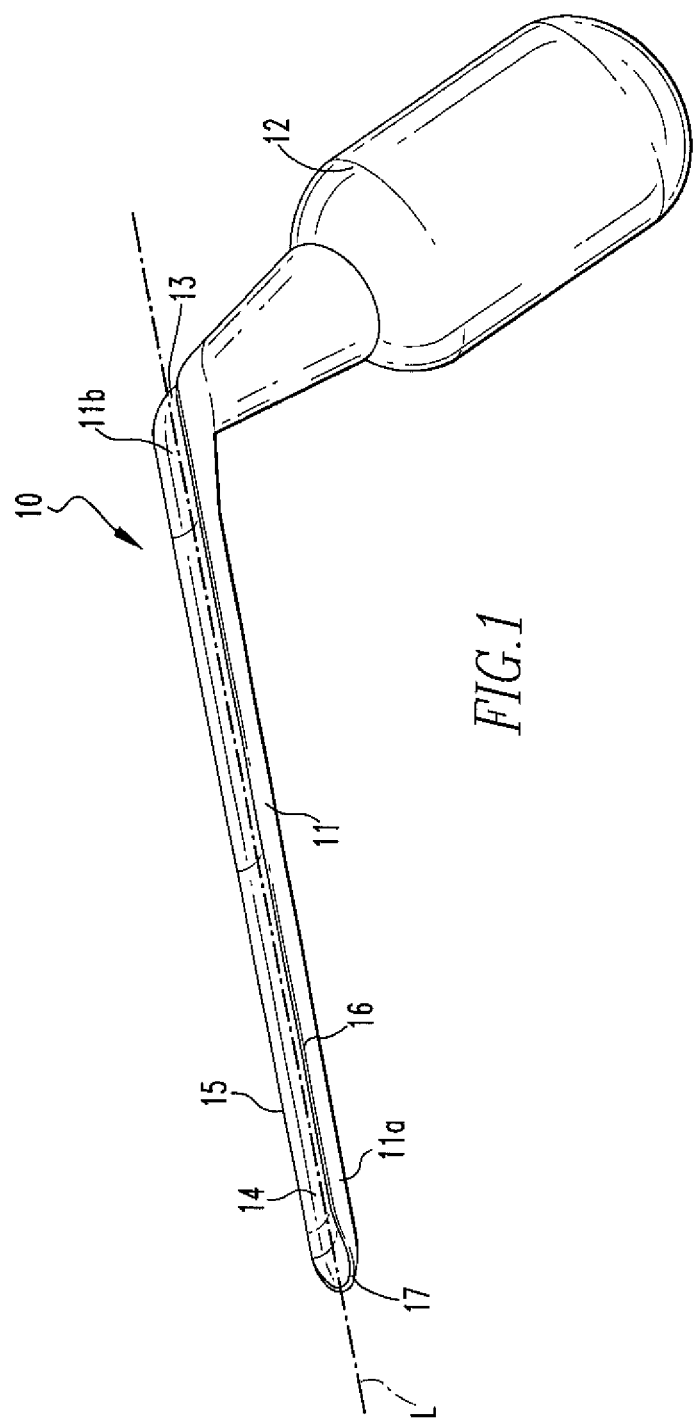
FIG. 1 shows a perspective view of an embodiment of the cannula of the present disclosure.

FIG. 1 shows the cannula 10 of the present disclosure. The cannula 10 includes a shaft 11 having a distal end 11a and a proximal end 11b and a handle 12 coupled to the proximal end 11b of the shaft 11. The handle 12 projects at an angle from a longitudinal axis L of the shaft 11. The shaft 11 includes an opening or slot 13 extending from the proximal end 11b to the distal end 11a of the shaft 11. In addition, the shaft 11 includes a round bottom 14 and two side walls 15, 16, thereby forming a semi-circular cross-section.

Figure 2:
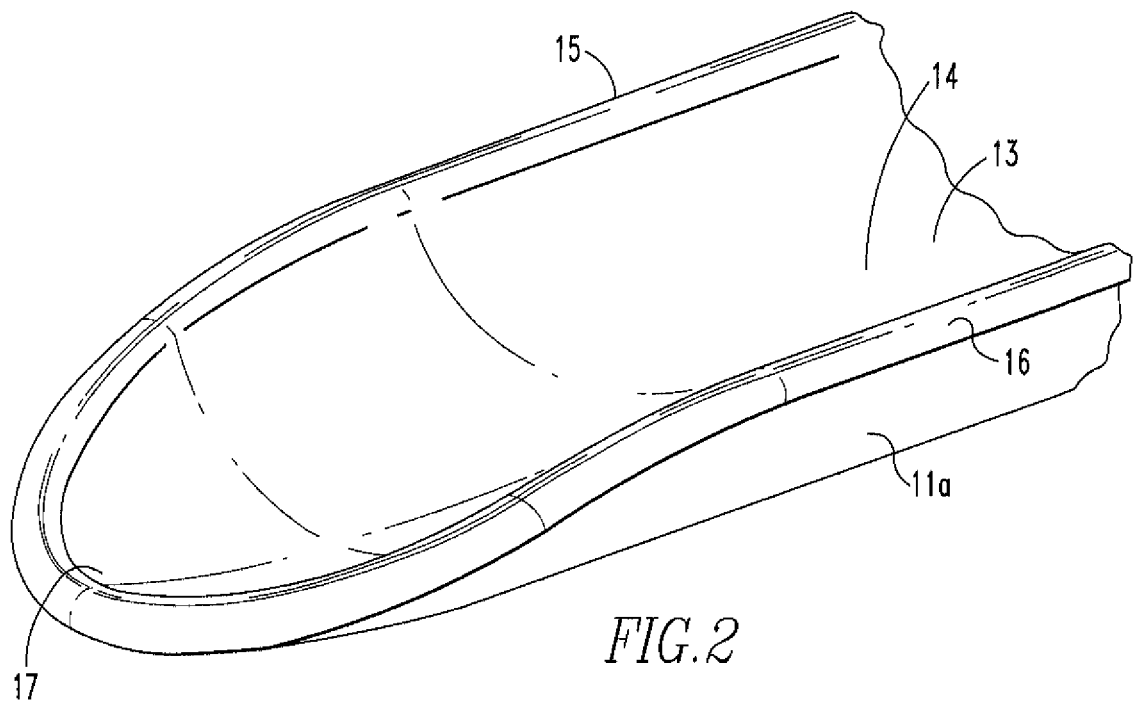
FIG. 2 shows an enlarged view of the tip of the shaft of the cannula of FIG. 1.
Figure 3:
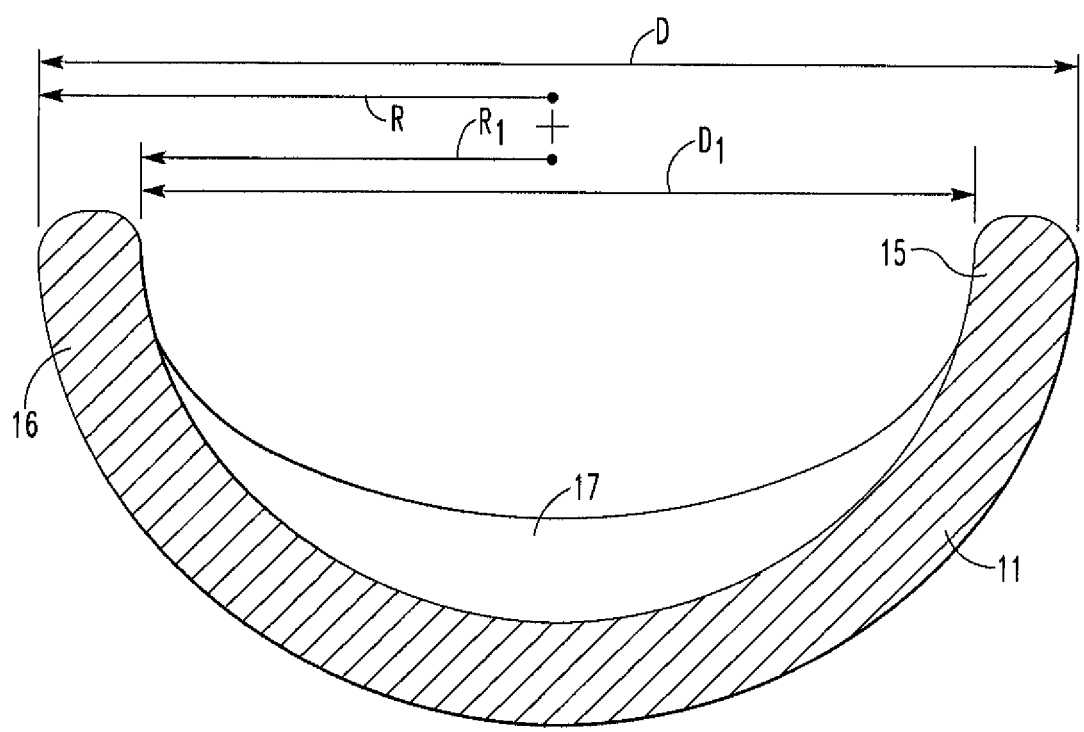
FIG. 3 shows a cross-sectional view of the shaft of the cannula of FIG. 1.
Figure 4:
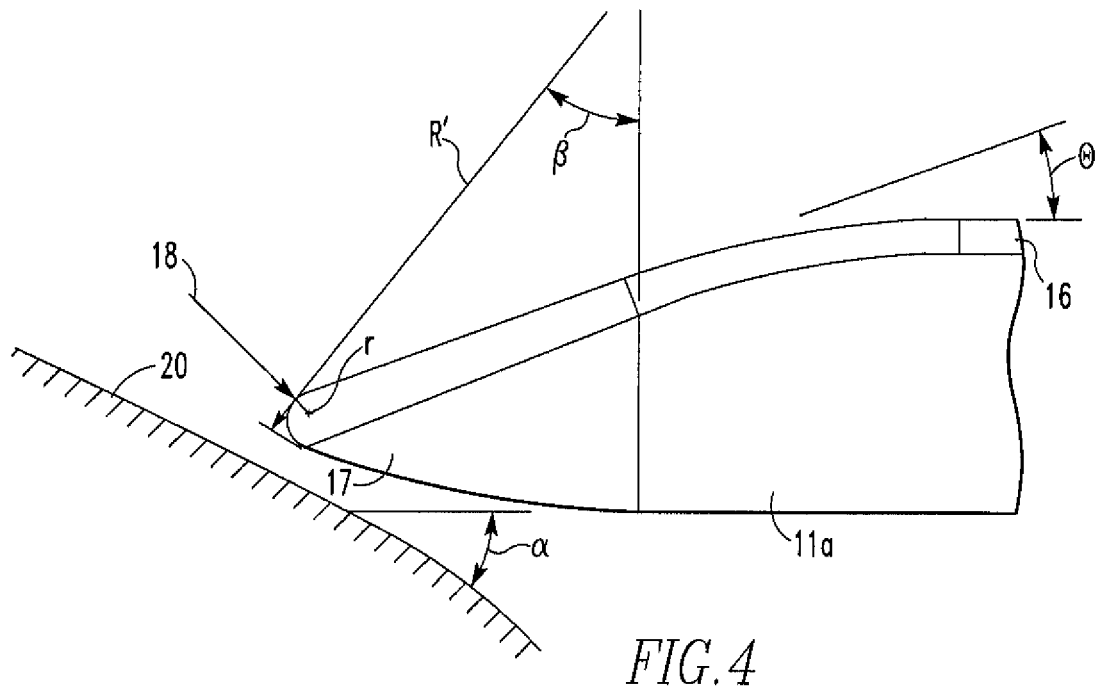
FIG. 4 shows a side view of the tip of the shaft of the cannula of FIG. 1 during insertion of the tip into tissue during surgery.

As shown in FIGS. 2-4, the distal end 11a of the shaft 11 includes a tip 17 having a spherical radius. FIG. 3 shows a cross sectional view of the shaft 11 having a shaft outer diameter D and a shaft outer radius R. As shown in FIG. 4, the spherical radius R' of the tip 17 is formed through included angle β, which is equal to or greater than the cannulas insertion angle α into a tissue surface 20, such as the articular cartilage surface of the acetabular cup, during hip arthroscopy. The spherical radius R' may or may not be equal to the outer radius R of the shaft 11. The angle β is about 30°. The spherical radius R' is truncated by its intersection with a cut-off angle Θ, resulting in a thick wall with a full radius edge 18. The cut-off angle Θ is about 20° and the radius r of the edge is about 0.015 inches. The shaft outer diameter D is about 0.310 inches and the shaft inner diameter $D_1$ is about 0.250 inches.

The semicircular shaft 11 is made from a round rod by hollowing the rod, via the use of a drill or other hollowing device, and then separating the rod into two halves. The spherical radius tip 17 is then formed according to the dimensions described above. The shaft 11 includes a biocompatible material, such as stainless steel, or other biocompatible material known to one of skill in the art. The handle 12 is shown as having a generally cylindrical shape, but may have any other shape known to one of skill in the art. In addition, the handle 12 is made from a material similar to the material of the shaft or other material known to one of skill in the art. The handle 12 and shaft 11 are coupled via known processes in the art.

Figure 5:
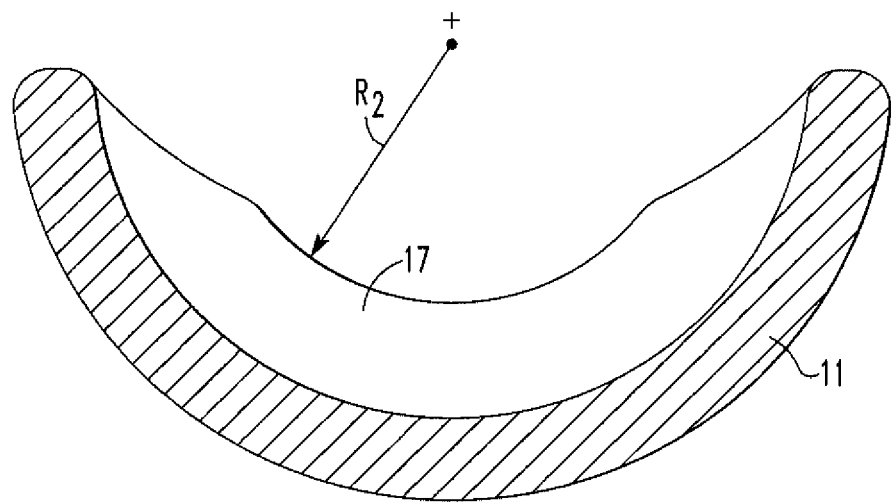
FIG. 5 shows a cross-sectional view of a shaft of an alternative embodiment of the cannula of the present disclosure.

FIG. 5 shows a cross-sectional view of an alternative embodiment of the cannula shaft 11. The spherical radius tip 17 may be modified to minimize point loading of instruments sliding above it. As shown in FIG. 5, especially when compared to FIG. 3, a smaller radius $R_2$ may be created with it axis generally parallel to the longitudinal axis of the shaft 11. This would spread out the contact point between the instrument and the tip 17 to minimize pressure between the tip 17 and the instrument being passed.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A cannula comprising:
a shaft comprising a semi-circular cross-section defining a longitudinal axis, a distal end and a proximal end, the distal end comprising an open tip that includes a spherical radius that is formed through and angle $\beta$, wherein the angle $\beta$ extends up to an intersection with a cut-off angle, the cut-off angle oriented at a 20 degree angle relative to the longitudinal axis and the angle $\beta$ is about 30 degrees, wherein the open tip is configured to minimize damage to adjacent tissue while guiding a medical instrument into a joint area; and
 a handle coupled to the proximal end of the shaft, and wherein the tip includes an edge with a radius.

2. The cannula of claim 1 wherein the spherical radius of the tip is equal to an outer radius of the shaft.

3. The cannula of claim 1 wherein the edge has a radius of about 0.015 inches.

4. The cannula of claim 1 wherein the semi-circular cross section defines an outer radius of about 0.155 inches.

5. The cannula of claim 4 wherein the shaft includes an inner radius defining an elongate channel, the inner radius being about 0.125 inches.

6. The cannula of claim 1 wherein the cut-off angle defines a continuous angle that extends up to and including a distal-most end of the cannula.

7. The cannula of claim 1 wherein the angle $\beta$ is equal to or greater than a cannula insertion angle $\alpha$ into the tissue surface.

8. A method of performing arthroscopic surgery comprising:
 providing a cannula into a joint area of the body such that a distal end is inserted into a tissue surface within the joint at an angle $\alpha$ relative to the tissue surface, the cannula comprising a shaft defining a semi-cylindrical cross section, a distal end, a proximal end and a longitudinal axis extending there between, and a handle coupled to the proximal end of the shaft, the distal tip defined by a spherical radius formed through angle $\beta$ that is equal to or greater than angle $\alpha$, wherein the spherical radius is truncated by its intersection with a cut-off angle that is continuously oriented at an oblique angle with respect to the longitudinal axis; wherein a portion of the shaft from the proximal end to the tip consists of one outer diameter and one inner diameter and a wall with a radiused edge;
 inserting a medical instrument through the cannula and into the joint area; and
 performing a surgical repair in the joint area.

9. The method of claim 8 wherein angle $\alpha$ is about 30°.

10. The method of claim 8 wherein the angle $\alpha$ is greater than about 30°.

11. The method of claim 8 wherein the cut-off angle defines a continuous angle that extends up to and including a distal-most end of the cannula.

12. The method of claim 8 wherein the cut-off angle is 20 degrees.

13. A cannula comprising:
 a shaft defining a semi-annular cross section having an elongate opening, the elongate opening defining a first side of the shaft, the shaft including a distal end, a proximal end and a longitudinal axis, and wherein the distal end has an open tapered tip portion, defined by a cut-off angle extending along the shaft first side, oriented at a 20 degree angle relative to the longitudinal axis and a spherical radius on a second opposing side of the shaft, the cut-off angle truncating the spherical radius so that the spherical radius is formed through angle $\beta$, wherein the spherical radius and cut-off angle intersecting at a radiused edge along the open tip portion; and
 a handle coupled to the proximal end of the shaft.

14. The cannula of claim 13 wherein the cut-off angle and spherical radius both extend up to and including a distal-most end of the cannula.

15. The cannula of claim 13 wherein the cut-off angle defines a continuous angle that extends up to and including a distal-most end of the cannula.

16. The cannula of claim 13 wherein the angle $\beta$ is equal to or greater than 30 degrees.

* * * * *